United States Patent

Miller et al.

[11] Patent Number: 5,159,563
[45] Date of Patent: * Oct. 27, 1992

[54] CRACK DETECTION METHOD FOR OPERATING SHAFT

[75] Inventors: William H. Miller, Loudonville, N.Y.; Warren R. Brook, Medford, N.J.

[73] Assignee: REM Technologies, Inc., Schenectady, N.Y.

[*] Notice: The portion of the term of this patent subsequent to Dec. 4, 2007 has been disclaimed.

[21] Appl. No.: 585,884

[22] Filed: Sep. 19, 1990

Related U.S. Application Data

[63] Continuation-in-part of Ser. No. 323,313, Mar. 14, 1989, Pat. No. 4,975,855.

[51] Int. Cl.$^5$ .............. G06F 15/20; G08B 21/00; G01H 17/00
[52] U.S. Cl. .................... 364/507; 73/579; 73/660; 364/551.02; 340/683
[58] Field of Search .......... 364/507, 588, 550, 551.02; 340/679, 680, 683; 73/579, 581, 659, 660, 622

[56] References Cited

U.S. PATENT DOCUMENTS

| | | | |
|---|---|---|---|
| 3,411,344 | 11/1968 | Lloyd | 73/67.2 |
| 4,195,528 | 4/1980 | Takahashi | 73/579 |
| 4,342,229 | 8/1982 | Massa | 73/579 |
| 4,380,172 | 4/1983 | Imam et al. | 73/659 |
| 4,408,294 | 10/1983 | Imam et al. | 364/508 |
| 4,559,600 | 12/1985 | Rao | 364/551.01 |
| 4,628,261 | 12/1986 | Hüschelrath et al. | 364/507 |
| 4,685,335 | 8/1987 | Sato et al. | 73/660 |
| 4,689,993 | 9/1987 | Slettemoen | 73/579 |
| 4,750,134 | 6/1988 | Hüschelrath et al. | 364/507 |
| 4,751,461 | 6/1988 | McWhirter et al. | 364/507 |
| 4,751,657 | 6/1988 | Imam et al. | 364/508 |
| 4,803,639 | 2/1989 | Steele et al. | 364/507 |
| 4,805,457 | 2/1989 | Oates et al. | 73/572 |
| 4,817,016 | 3/1989 | Thompson et al. | 364/507 |
| 4,821,204 | 4/1989 | Hüschelrath | 364/507 |

Primary Examiner—Joseph L. Dixon
Attorney, Agent, or Firm—Heslin & Rothenberg

[57] ABSTRACT

The presence, size and location of a crack in a shaft is determined by comparing actual measured natural frequencies of the operating shaft system with the results of an analytical model. From a multi-station analytical model of an uncracked operating shaft system, natural frequencies and associated mode shapes are derived. A suspected axial location of a crack is defined, and a natural frequency of interest is selected which has an associated mode shape exhibiting significant localized bending at the suspected axial location of the crack and at a site of response measurement. The analytical model is modified to include a representation of an asymmetric crack at the suspected crack location. A predicted split and downward shift of a lateral natural frequency of interest as a function of crack depth and/or a predicted downward shift of a torsional natural frequency of interest as a function of crack depth is calculated from the modified model. The actual shaft system is subjected to an operating force excitation, and vibrational response measurements are taken with strain gages and then output through a short range telemetry system. A fast Fourier transform analyzer derives frequency response spectra from the measurements which indicate the actual natural frequencies of the shaft system. A comparison of actual natural frequency(s) in the region near the natural frequency of interest with frequency values predicted by the modified model is employed to determine the presence and severity of a crack in the shaft.

43 Claims, 14 Drawing Sheets

CRACK DETECTION METHOD FOR OPERATING SHAFT

RELATED APPLICATION

This application is a continuation-in-part of application Ser. No. 07/323,313, filed Mar. 14, 1989, now U.S. Pat. No. 4,975,855.

BACKGROUND OF THE INVENTION

This invention relates in general to the field of non-destructive testing and more particularly to a method for determining the presence, size and location of a crack in an operating (e.g. rotating) shaft. For purposes of this description, a crack is defined as any non-designed physical discontinuity and the term shaft encompasses any axially extending structure which has a length considerably larger than its cross sectional dimension. Such structures take a wide variety of forms and are employed as motor rotors, shafts of pumps, generators, compressors, turbines, etc. Although the present invention is applicable to any such shafts, it will be presented, by way of example, primarily in the context of detecting a crack in an on-line (i.e. operating) reactor coolant pump shaft of a pressurized water reactor (PWR).

Nuclear reactors have been operating and producing useful electricity for many years. Within the last few years, several plants have found cracks in the reactor coolant pump shaft near the thermal barrier.

The large reactor coolant pump of a PWR circulates water out of the reactor vessel into steam generators which in turn pass steam to a steam turbine. The reactor coolant pump system consists of a vertical pump with a vertical motor mounted on the pump from above. In a typical design, the entire shaft system hangs vertically and is supported by a thrust bearing located on the top of the vertical motor. The pump system usually has an overhung impeller and an axial suction inlet from below the pump. The cooling water exits the pump through a single radial discharge in the horizontal direction. A net radial force is developed on the rotating shaft during the operation of the pump. This unidirectional unbalanced force applied to the rotating pump shaft can lead to a fatigue crack in the shaft and subsequent pump shaft failure.

The consequences of an unforeseen pump shaft failure can be dire. A nuclear facility can lose millions of dollars a day in revenues from an unscheduled outage. Further, these pumps are responsible for cooling the reactor, so a failure might lead to a potential melt-down situation and the associated radiation hazard. Since pump shaft replacement is an expensive, time consuming project, it is highly desirable to be able to discover the crack condition early and thus have time to plan and schedule the replacement.

A reliable, early warning method for the on-line identification and quantification of shaft cracks, has not theretofore been available. Existing devices typically collect and analyze vibrational data off a running machine. However, operating vibrational data in the form of 1X (operating speed) and 2X (twice operating speed) amplitude and phase data is usually clouded with electrical, mechanical and background noise such that little useful information relative to the shaft condition can be obtained.

Field studies show that with existing measurement equipment, cracks are not recognizable until they reach a depth of at least 20% of the shaft diameter. The inability to detect a crack at earlier stages, can leave insufficient time to schedule the manpower, parts, etc. required to replace the shaft.

Static test methods which require the shaft under test to be at rest are necessarily limited in their frequency of application and, therefore, in the availability of test results.

A need thus exists for a reliable, on-line shaft crack detection method which can identify the presence, size, and location of a shaft crack in the early stages of crack development and which allows monitoring of crack propagation on a continual basis or whenever desired, during machine operation. The test method has to be applied on site, in a non-destructive fashion, and with minimal radiation exposure to the test personnel. Further complicating the situation is the fact that only limited access to the reactor coolant pump shaft is available.

SUMMARY OF THE INVENTION

This need is satisfied and the deficiencies of the prior art overcome, in accordance with the principles of the present invention, through the application of a modal analysis test method to an operating shaft system. By taking advantage of the amplification associated with natural frequencies of the shaft, the new test method is able to identify the presence of a crack having a radial depth on the order of 5% of the pump shaft diameter in the region of the crack. This provides a significantly earlier warning of impending shaft failure than existing techniques, allowing for a planned replacement during a scheduled outage. The new method, when utilized to monitor the shaft for crack initiation and subsequent propagation will enable nuclear power plant operators to avoid difficult shutdown situations and costly unscheduled outages. The test is applied utilizing vibratory forces present during operation of the shaft system and thus requires no additional or special shaft excitation. Further, the method allows vibrational response to be measured using readily available strain gages or other suitable means mounted on any portion of the shaft system, and yet is capable of detecting a crack located anywhere along the axis of the shaft. Following initial instrumentation of the shaft system, test data is available at any time without interrupting the revenue generating operation of the plant. Compared to static tests, the present invention also sharply reduces set-up time, trained manpower requirements, and personnel exposure to process hazards such as radiation.

The method of the present invention utilizes an analytical model of the shaft system under test to guide and interpret the results of a vibrational test applied to the actual shaft system. In the vibrational test, the shaft system's response to operating system force excitation is measured for lateral analysis and/or for torsional analysis. A correlation between the actual natural frequency(s) exhibited by the shaft system in response to the operating system force excitation, and a predicted split and shift in a lateral analysis natural frequency of interest and/or a predicted downward shift in a torsional analysis natural frequency of interest provided by the analytical model, is used to identify the presence and severity of a crack in the shaft.

In accordance with one aspect of the present invention, a multi-station structural dynamics model of an uncracked operating shaft system is employed to derive lateral analysis and/or torsional analysis natural frequencies and associated mode shapes. A probable or suspected axial location of a crack is determined and a natural frequency of interest for lateral and/or torsional analysis is selected having a mode shape which exhibits significant localized bending at the probable axial location of the crack and a site of response measurement. The model is then modified to incorporate a representation of an asymmetric crack at the probable axial location and the resultant split and shift of a lateral analysis natural frequency of interest and/or shift in a torsional analysis natural frequency of interest as a function of crack depth is determined. Excitation forces due to machine operation excite the shaft system under test and measurements are taken of the shaft system vibrational response at multiple response measurement locations along the circumference of the shaft for lateral and/or torsional analysis. The measurements are processed, preferably by a fast Fourier transform analyzer, to determine the actual natural frequency(s) of the shaft system in the region of the frequency of interest. A correlation between the actual natural frequency(s) and the shift and split in the lateral analysis natural frequency of interest and/or the shift in the torsional analysis natural frequency of interest predicted by the analytical model, provides an indication of shaft crack presence and severity.

In a further aspect of the invention, the crack is modeled by determining an equivalent diameter and effective length of a right circular section for a stiff axis extending substantially parallel to the crack wave front and a soft axis extending along the depth of the crack for lateral analysis, and for a polar axis extending longitudinally through the center of the shaft for torsional analysis. In another aspect of the invention, the analytical model of the shaft system can optionally be verified by applying a roving modal analysis to a physical model of the shaft system. In a further aspect of the invention, strain gages can be advantageously employed to detect vibrational response and a short range telemetry system used to transmit vibration response signals from the operating shaft system.

The test method of the present invention may be advantageously implemented in a lateral analysis mode and/or a torsional analysis mode. The latter involves modeling of the effective mass of water in the pump bowl in addition to the entire rotatable structure; the former further involve modeling of surrounding bearings, seals and frame, plus the effect on the shaft system of the force created by unequal pressure in the pump bowl during operation. The invention also contemplates independent or integrated application of the analytical and experimental portions of the modal analysis method.

BRIEF DESCRIPTION OF THE DRAWINGS

These and other objects, features and advantages of the invention will be more readily understood from the following detailed description when read in conjunction with the accompanying drawings, in which.

DETAILED DESCRIPTION

Figure 1:
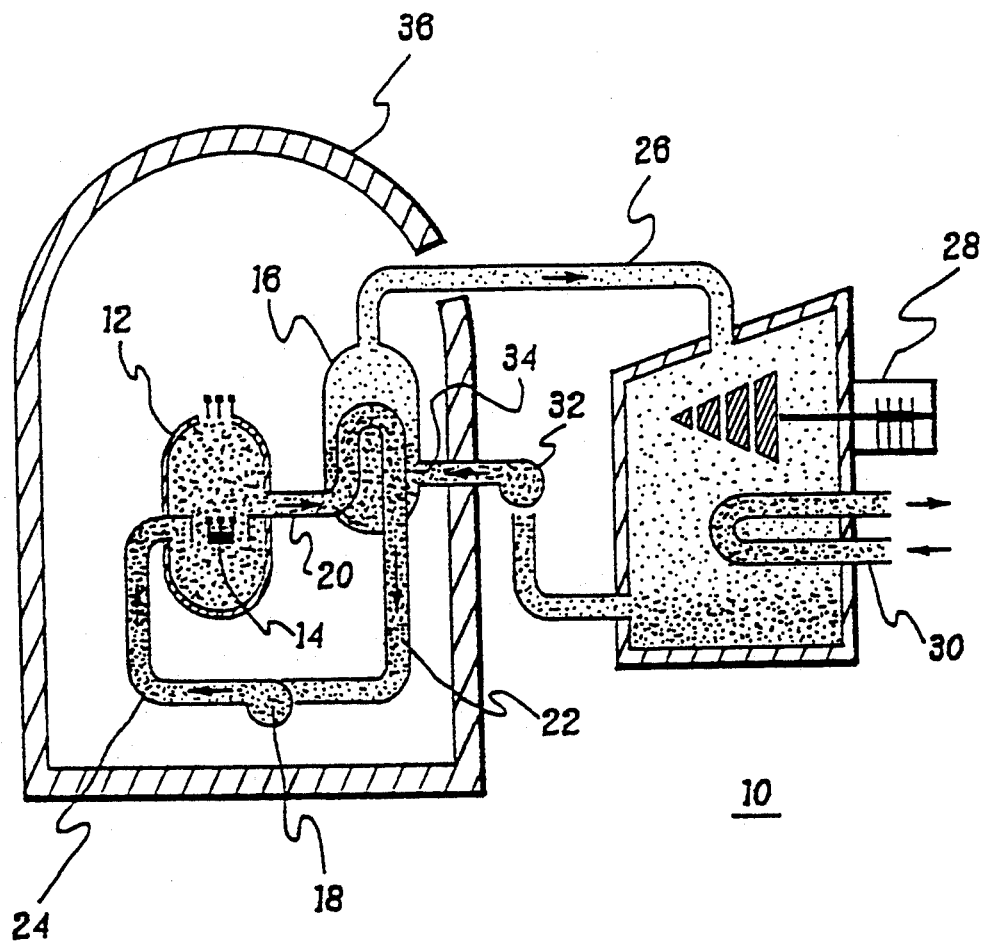
FIG. 1 is a simplified schematic representation of a typical pressurized water reactor (PWR) nuclear power plant.

A schematic of a typical pressurized water reactor (PWR) nuclear power plant 10 is shown in FIG. 1. In operation, high temperature, high pressure water is pumped from the reactor vessel 12 (from around the reactor core 14) to a steam generator (heat exchanger) 16 by the reactor coolant pump 18. A continuous loop of piping 20, 22, 24 interconnects the pressure vessel 12, steam generator 16 and reactor coolant pump 18, as shown. Steam generator 16 in turn passes steam along steam line 26 to a steam turbine generator 28. Finally, cooling water from a condenser 30 is pumped by pump 32 into the inlet 34 of steam generator 16.

Figure 2:
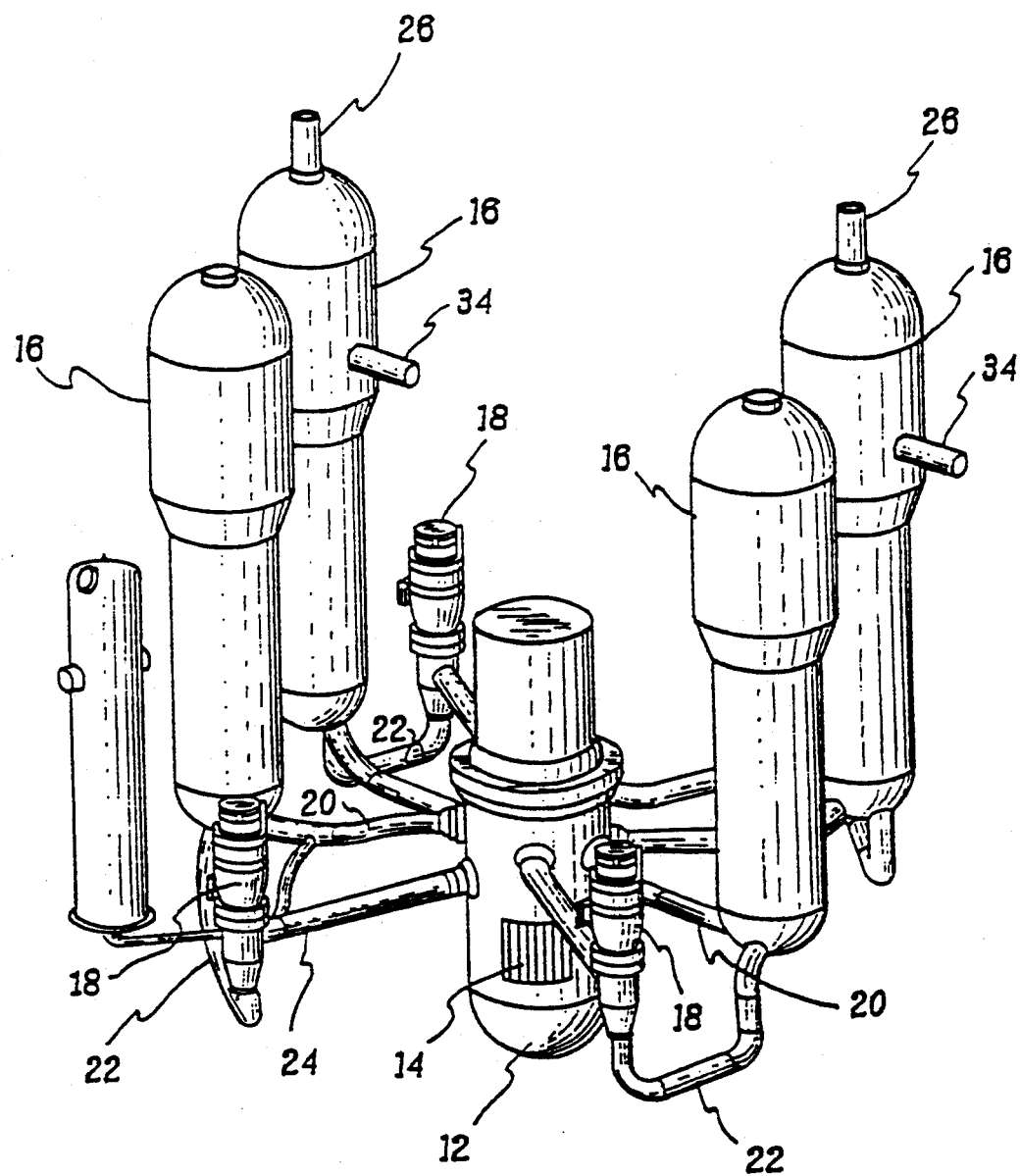
FIG. 2 is a more detailed illustration of a reactor coolant system for a PWR.

FIG. 2 is a more detailed sketch of the reactor coolant system for the PWR which is housed inside the containment structure 36 (FIG. 1). Four reactor coolant pumps (RCPs) 18 and associated steam generators 16 surround and are interconnected with the reactor vessel 12. If one of the RCPs 18 should fail and be shut down because of a crack in the pump shaft, the nuclear power plant may still be able to operate but obviously at a reduced load and with significantly reduced revenue generated. The present invention relates to an on-time early warning method for detecting shaft cracks which will enable plant operators to avoid unscheduled outages.

Figure 3:
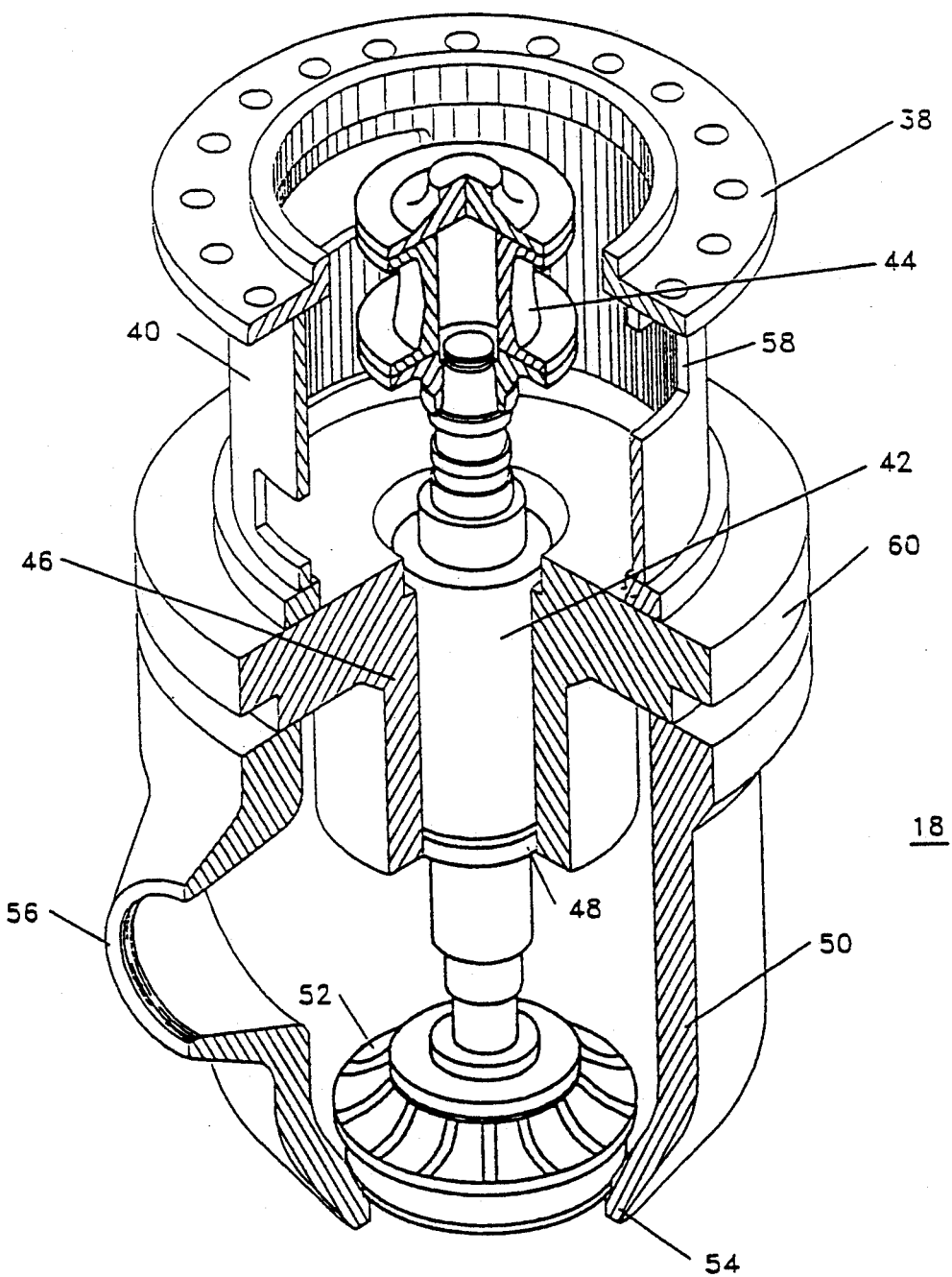
FIG. 3 is a partially broken away sectional view of a reactor coolant pump.
Figure 4:
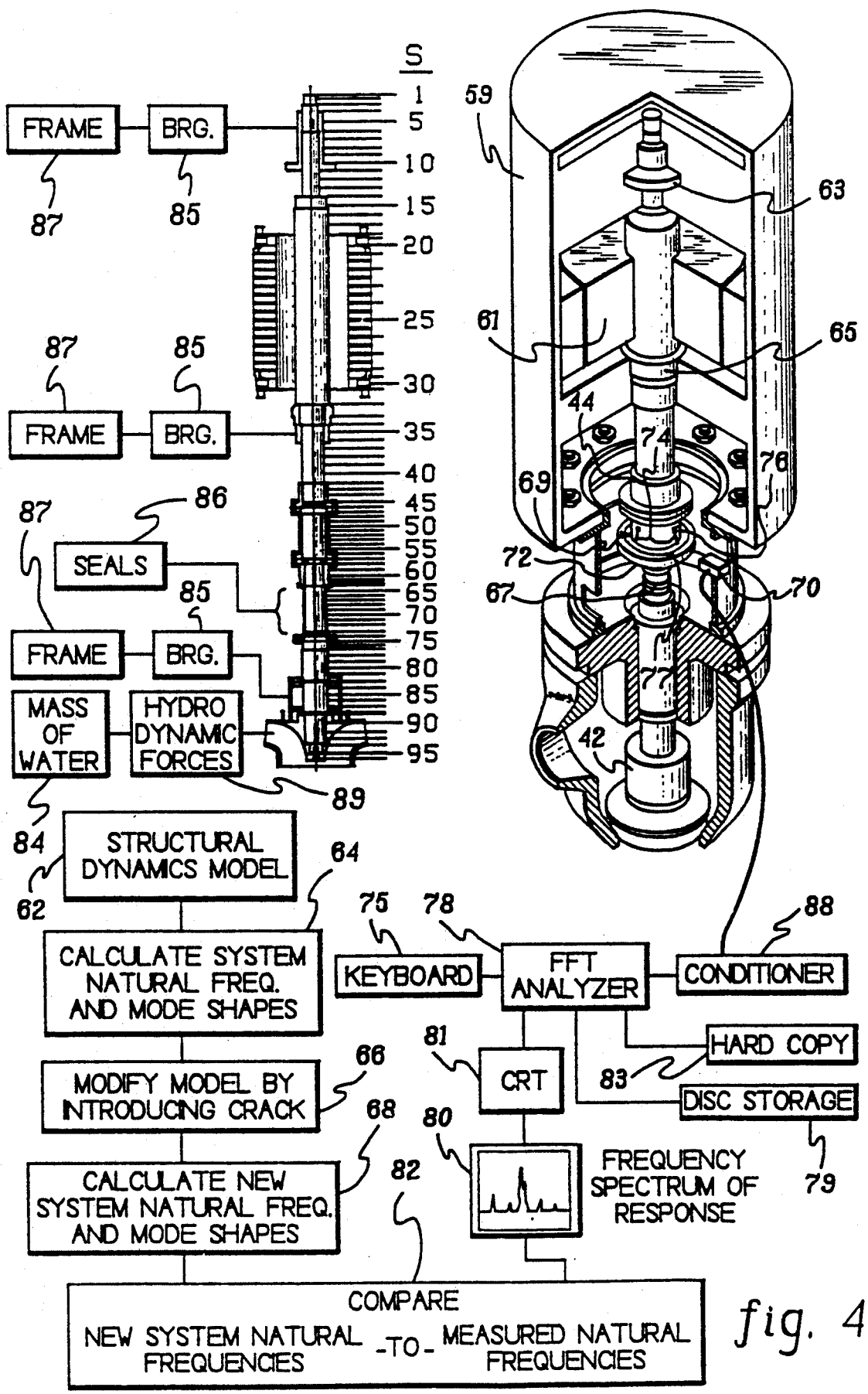
FIG. 4 is schematic depiction, partly in block diagram form, of the general modal analysis test method of the present invention.

FIG. 3 is a sectional, partially broken away view of a typical reactor coolant pump 18. A drive motor (not shown) is mounted on flange 38 atop motor support housing 40. The motor's rotor is connected to the pump shaft 42 by a spool piece coupling 44. (Drive motor 59, motor rotor 61, and motor bearings 63 and 65 are shown in FIG. 4.) Referring still to FIG. 3, a radial guide bearing 46 surrounds a portion of pump shaft 42 at a location above a thermal barrier 48. Thermal barrier 48 serves to isolate the bearing area from the extremely high temperatures of the water within casing 50. An impeller 52 is mounted at the lower end of shaft 42 by a set of bolts (not shown).

Water from the steam generator enters vertically upward into the suction nozzle 54 of the reactor coolant pump 18. The pump discharge is horizontal through discharge nozzle 56 into the reactor vessel. During operation of the pump, discharge flow causes a net pressure differential across the pump shaft 42. Since the pump shaft is rotating in the pump casing 50, a given point on the shaft is subjected to a cyclic force. This force is reacted by the pump shaft 42 on the guide bearing 46. Generally the thermal barrier and the guide bearing journal have a sleeve shrunk on the shaft at these locations. In some cases, the sleeve is further secured through the use of a shear pin, or welding, or both locking mechanisms (not shown). The shear pin and welding give rise to stress concentrations which in combination with the cyclic force can result in the formation of a shaft crack, often just below the thermal barrier. Continued operation of the pump will cause the crack to propagate. Shaft cracks have occurred in operating nuclear power plants and have apparently gone undetected until the pump impeller 52 broke off the shaft 42.

The new modal test method of the present invention can be advantageously employed to identify the presence, size and location of a crack in a vertical reactor coolant pump shaft or shaft system during operation thereof. The method recognizes that the only access to the shaft system is through the cutouts 58 in the motor support housing 40 which is mounted on the main flange 60 and encloses the coupling 44. No other access to the pump shaft 42 is readily available. The method of the present invention enables the shaft system response to operating force excitation to be obtained through the motor stand access holes 58, without any disassembly.

FIG. 4 presents an overview of the modal analysis test method of the present invention, as it might be applied to the detection of cracks in a RCP shaft. As shown, a multi-station structural dynamics or analytical model 62 of the operating shaft system, with an uncracked shaft, is developed. From this model the shaft system's lateral and/or torsional natural frequencies and associated mode shapes are calculated (box 64). The model is then modified by introducing a representation of a crack at a suspected or probable axial location along the shaft (box 66). From the modified model, new system lateral and/or torsional natural frequencies and mode shapes are calculated (box 68). The new lateral natural frequencies reflect a shift and split of the original natural frequencies caused by the introduction of the crack. The new torsional natural frequencies reflect a downward shift of the original natural frequencies caused by the introduction of the crack.

Actual or measured natural frequencies of the shaft system are determined by measuring the vibrational response of the shaft system due to the force excitation present in the machine during operation. Response readings are taken by strain gages 74 fastened to coupling 44 and transmitted to a surrounding stationary antenna 72 by a short range telemetry system. Signals from antenna 72 are conditioned by conditioner 88 and then processed by a fast Fourier transform (FFT) analyzer 78. An input keyboard 75, disc storage device 79, CRT monitor 81 and hard copy printer 83 can be advantageously connected to FFT analyzer 78. The analyzer provides frequency response spectra 80, the peaks of which identify the measured lateral and/or torsional natural frequencies of the actual shaft system. A comparison of these measured lateral and/or torsional natural frequencies with the new system lateral and/or torsional natural frequencies calculated from the modified analytical model is used to determine the presence and severity of a crack in the shaft 42 (box 82).

The method of the present invention is applied to the RCP shaft system while the shaft 42 is rotating under operating conditions. The analytical model identifies a natural frequency of interest based on the axial locations of the suspected crack and the response measurement site of the shaft system. The modified model further predicts crack effect (split and shift) upon the lateral natural frequency of interest and/or crack effect (shift) upon the torsional natural frequency of interest as a function of crack depth. The analytical model thus serves as a road map for guiding the analysis of the actual vibrational test results. Further details and aspects of the method of the present invention will now be described in connection with the remaining drawing figures.

The method of this invention is based on the observation that there is a direct correlation between the existence of a crack and the crack's effect on the operating shaft system's lateral and torsional natural frequencies. A given operating shaft system will have a series of natural or resonant frequencies. If an asymmetric crack is introduced into the shaft, each of the lateral natural frequencies splits into two new, different lower frequencies. The lowest of the new frequencies is associated with a soft axis which extends along the depth of the crack; the other new frequency is associated with a stiff axis substantially parallel to the wave front of the crack. The reduction in value of lateral natural frequency and the separation between the two new frequencies can be correlated with the depth of the crack. The lateral natural frequency most affected by the modeled crack correlates to the axial location of the crack.

When an asymmetric crack is introduced into the shaft, each of the torsional natural frequencies shifts to a different lower frequency. The reduction in value of torsional natural frequencies can be correlated with the depth of the crack. The torsional natural frequency most affected by the modeled crack correlates to the axial location of the crack.

The modal analysis crack detection method of the present invention begins with an accurate multi-station analytical model of the operating shaft system under test (i.e. the entire rotatable structure, the effect of the water in the pump impeller, and, for lateral analysis, the surrounding bearings, seals and frame, and the effect of the pressure differential in the pump casing on the shaft system.) The analytical model should contain sufficient stations to ensure that the lateral and/or torsional natural frequencies of the shaft system can be calculated with a high degree of precision. Preferably, the accuracy provided by such a refined or enhanced model should be comparable to the frequency resolution of the FFT analyzer used in the experimental instrumentation of the shaft system. The inventors have discovered that a modeling criteria in which the separation between stations is no greater than one half of the local shaft system radius is desirable.

Figure 5A:
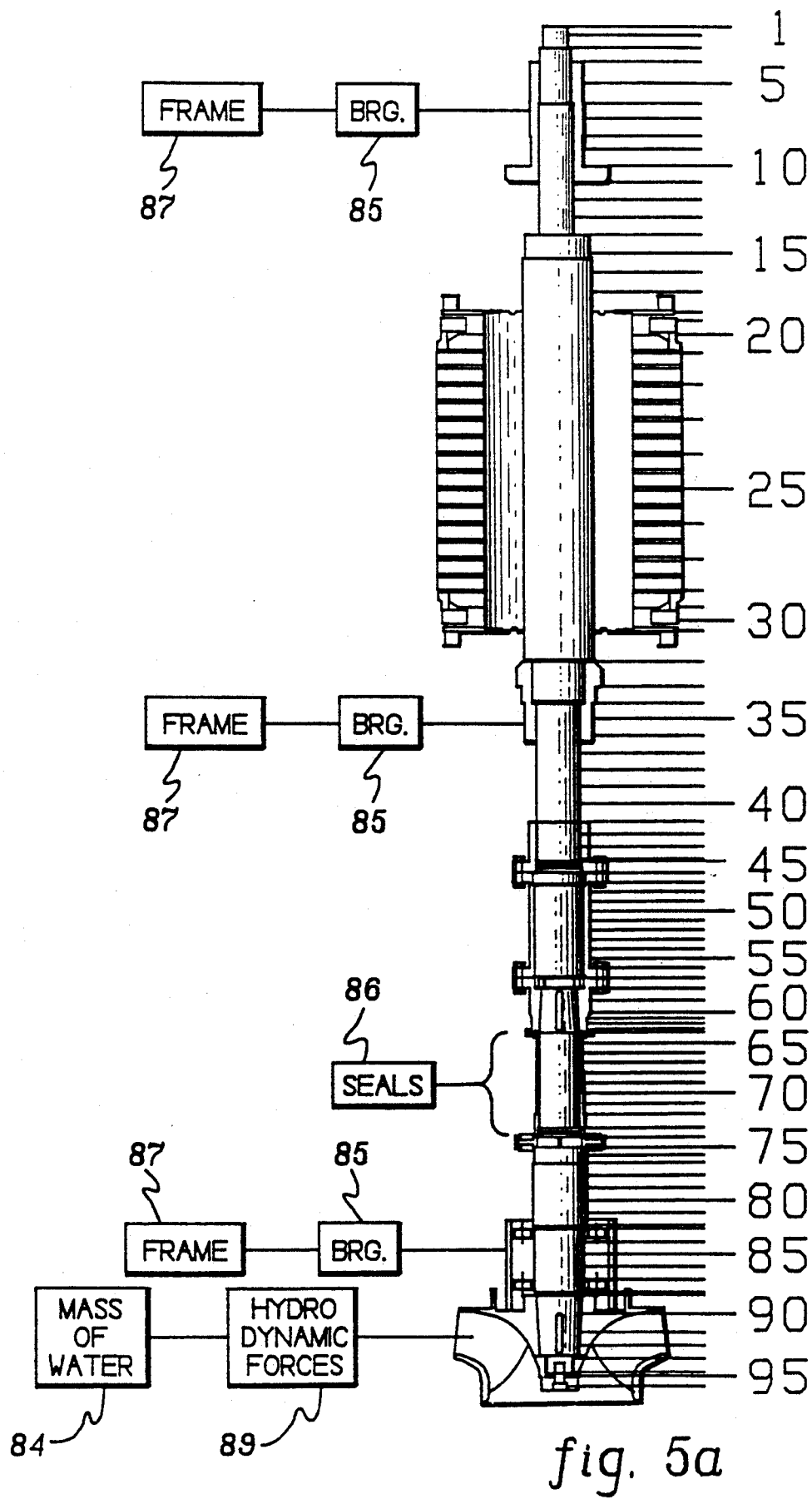
FIG. 5a is a graphical depiction of a multi-station structural dynamics model of a pump shaft system.

FIG. 5a schematically depicts multiple stations S1–S95 which might be used to model a RCP shaft system. The model includes a representation of the rotatable structural elements of the corresponding shaft system under test and an effective mass 84 at the impeller end of the shaft representative of the water in the pump impeller (i.e., a percentage of the mass of water contained in the volume of the impeller) for torsional analysis, plus bearings 85, seals 86, frame 87 and the water pressure differential producing force 89 for torsional analysis. Various rotor dynamics computer programs and publications are publicly available and can be used to model the uncracked operating shaft system of such pumps. Refer, for example, to "DYNAMICS OF DISTRIBUTED PARAMETER ROTOR SYSTEMS: TRANSFER MATRIX AND FINITE ELEMENT TECHNIQUES", a doctoral thesis by R. L. Ruhl, dated Jan., 1970 and available from University Microfilms, Inc. of Ann Arbor, Mich. as document number 70-12,646; "THE EFFECT OF DISC FLEXIBILITY ON ROTOR DYNAMICS", a doctoral thesis of J. A. Dopkin, dated Oct. 1972 and available from University Microfilms as document number 73-4739; NASA Report No. TN D-7385 "FORTRAN IV COMPUTER PROGRAM FOR CALCULATING CRITICAL SPEEDS OF ROTATING SHAFTS" by R. J. Trivisonno, dated Aug. 1973; CADENCE software available from Mechanical Technologies, Inc. of Albany, N.Y.; ANSYS finite element analysis program available from Swanson Analysis Systems Inc. of Houston, Pa.; "THE INFLUENCE OF HIGH PRESSURE OIL SEALS ON TURBO-ROTOR STABILITY" an American Society of Lubrication Engineers paper by R. G. Kirk and W. H. Miller, 1977; and "STABILITY AND DAMPED CRITICAL SPEEDS OF A FLEXIBLE ROTOR IN FLUID-FILM BEARINGS", J. W. Lund, ASME paper No. 73-Det.-103, 1973.

From such computer program models, the natural frequencies and associated mode shapes of the operating shaft system under test for lateral and/or torsional analysis can be derived, in known fashion. If desired, a physical model or sample of the shaft system under study can be subjected to a roving force modal analysis test, and/or a structural dynamics model of the shaft system at rest can be used in order to refine and/or verify the computer model predicted natural frequencies and mode shapes.

A suspected or probable axial location of a crack in the shaft under test is then defined. This location is obviously dependent upon the physical forces affecting the shaft in a particular application. As earlier indicated, in a RCP, the expected crack location is in the vicinity of the thermal barrier. A natural frequency of interest (lateral and/or torsional) is then selected from among the natural frequencies identified by the analytical model. The natural frequency having an associated mode shape which exhibits significant localized bending at both the probable axial location of the crack and the site of response measurement of the shaft system, is chosen as the natural frequency of interest.

Figure 5B:
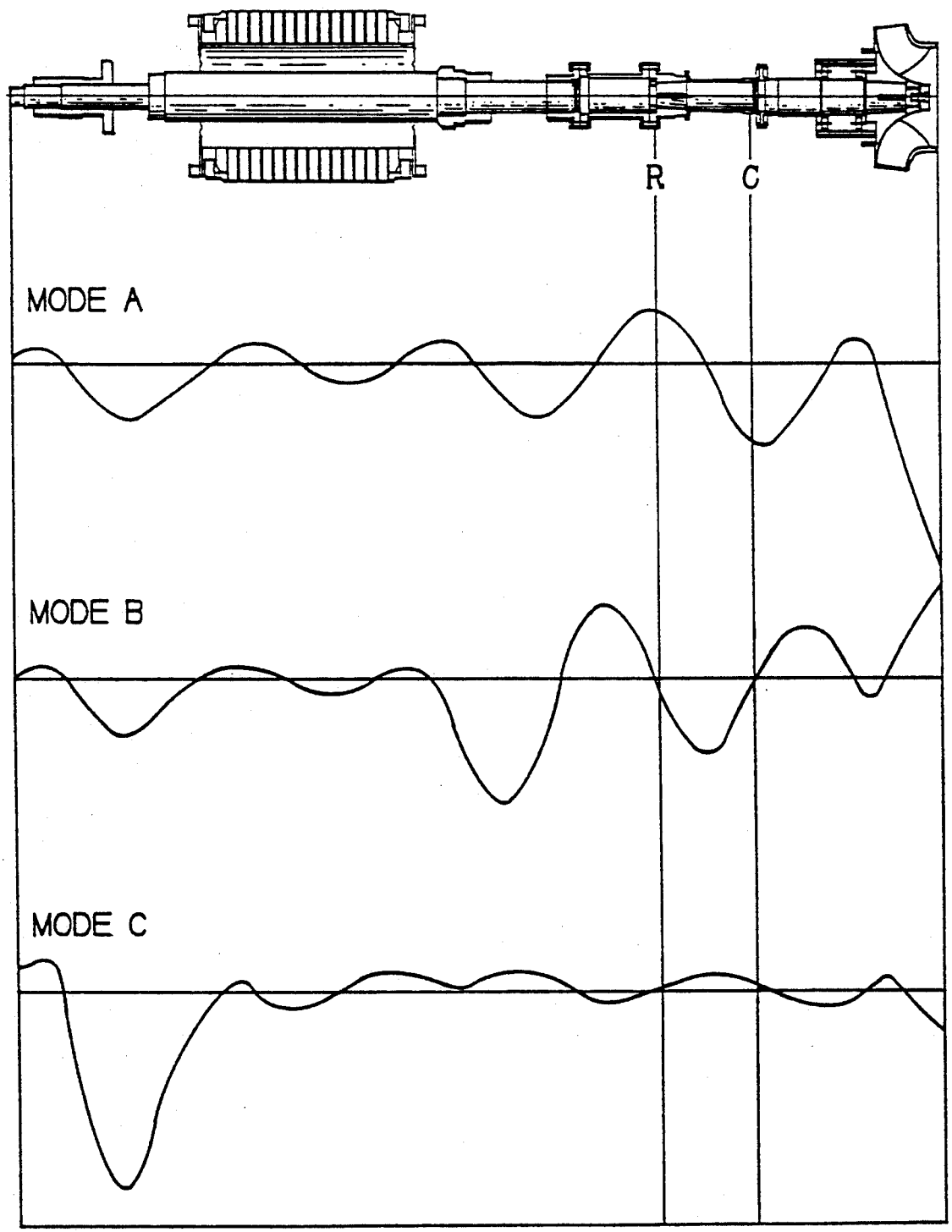
FIGS. 5b and 5c present illustrative lateral mode shapes and torsional mode shapes, respectively, associated with various natural frequencies for an uncracked shaft system, useful in understanding how a natural frequency of interest can be selected.
Figure 5C:
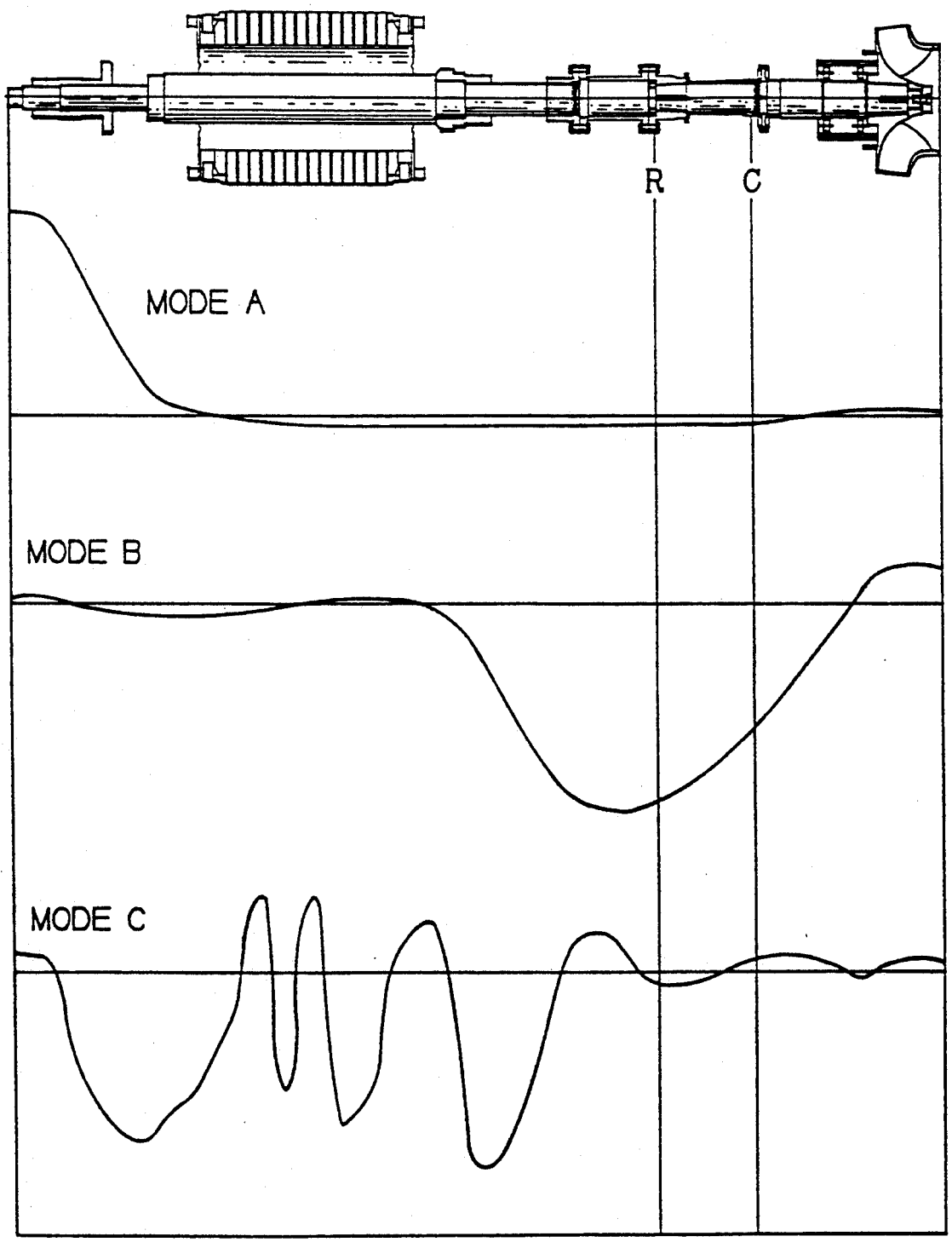

Various illustrative mode shape curves are presented in FIGS. 5B and 5C and will now be described in order to explain how a natural frequency of interest can be selected. High local bending is characterized in the lateral mode shape curves (FIG. 5b) by a large change in the slope of the curve. In the torsional mode shape curves (FIG. 5c) high local bending is characterized by areas of high positive or negative slope, (i.e. high rate of change of angular twist). Lateral mode A in FIG. 5b is of interest for crack analysis due to the high bending, and high displacement at both the suspected crack location "c", and the response measurement site "R". Modes B, and C are not of interest because both the suspected crack and the response measurement sites are located at points of low bending and low deflection in both modes. Torsional mode B in FIG. 5c is of interest for crack analysis due to the high torsional bending at the suspected crack location "c" and the response measurement site "R". Modes A, and C are not of interest because the angular displacement curves at the crack and response measurement sites do not show large slopes, therefore the bending is low at these points. The probable axial location of the crack also establishes the diameter D of the shaft for further study.

The new modal test method of the invention was developed so that a shaft system could be examined for a crack when access to the shaft was limited. The method enables regions of the shaft some distance from the response measurement site to be examined for cracks. This is accomplished by identifying a higher order natural frequency such that the mode selected has a region of high bending near the response measurement site and the suspected location of the crack.

Any position along the entire length of the shaft can be examined by using this technique. Each new position will require examining a different natural frequency and associated mode shape. Performing a natural frequency analysis of the operating shaft system allows for an analytical determination of the expected natural frequency of interest, mode shape and region of high bending in order to guide the experimental testing of the shaft system. The theory underlying the invention will now be briefly discussed.

The nature of a vibrating structure is such that it seeks the state of minimum potential energy. A structure undergoing vibration will dissipate energy through structural damping or hysteresis. It has been found that damping is encountered proportional to displacement but out of phase with the velocity of harmonic oscillation. This phenomenon can be described mathematically by:

$$[m]\ddot{u} + (1+ig)[K]\ddot{u} = B\sin Wt \tag{1}$$

where
 "m" represents mass;
 "ü" represents displacement coordinate;
 "g" is the structural damping coefficient which is usually less than 0.05;
 "K" represents shaft stiffness;
 "B" represents the magnitude of the forcing function; and
 "W" represents angular precession frequency.

The structural damping theory applies to the shaft crack detection method since it is the mechanism responsible for exciting orthogonal, closely spaced natural frequencies. The two orthogonal, primary modes of the cracked shaft, correspond to directions perpendicular to and parallel to the crack "wave front" 84 (see the cross-sectional representation of an asymmetric shaft crack of FIG. 6), and these directions are referred to as the soft axis and stiff axis, respectively.

By exciting the shaft system through its operation and rotation, two lateral natural frequencies can be found which are slightly below the lateral natural frequency of interest measured for an uncracked operating shaft system. Their frequency separation will be an indication of crack depth, a.

By exciting the shaft system through operation, a torsional natural frequency can be found which is slightly below the torsional natural frequency of interest measured for an uncracked operating shaft system. The frequency reduction will be an indication of crack depth, a.

In accordance with the principals of the present invention, the analytical model of the uncracked operating shaft system is modified to include a representation of an asymmetric crack at the suspected axial location. The theoretical basis and a preferred approach for so modifying the analytical model will now be discussed.

Figure 7:
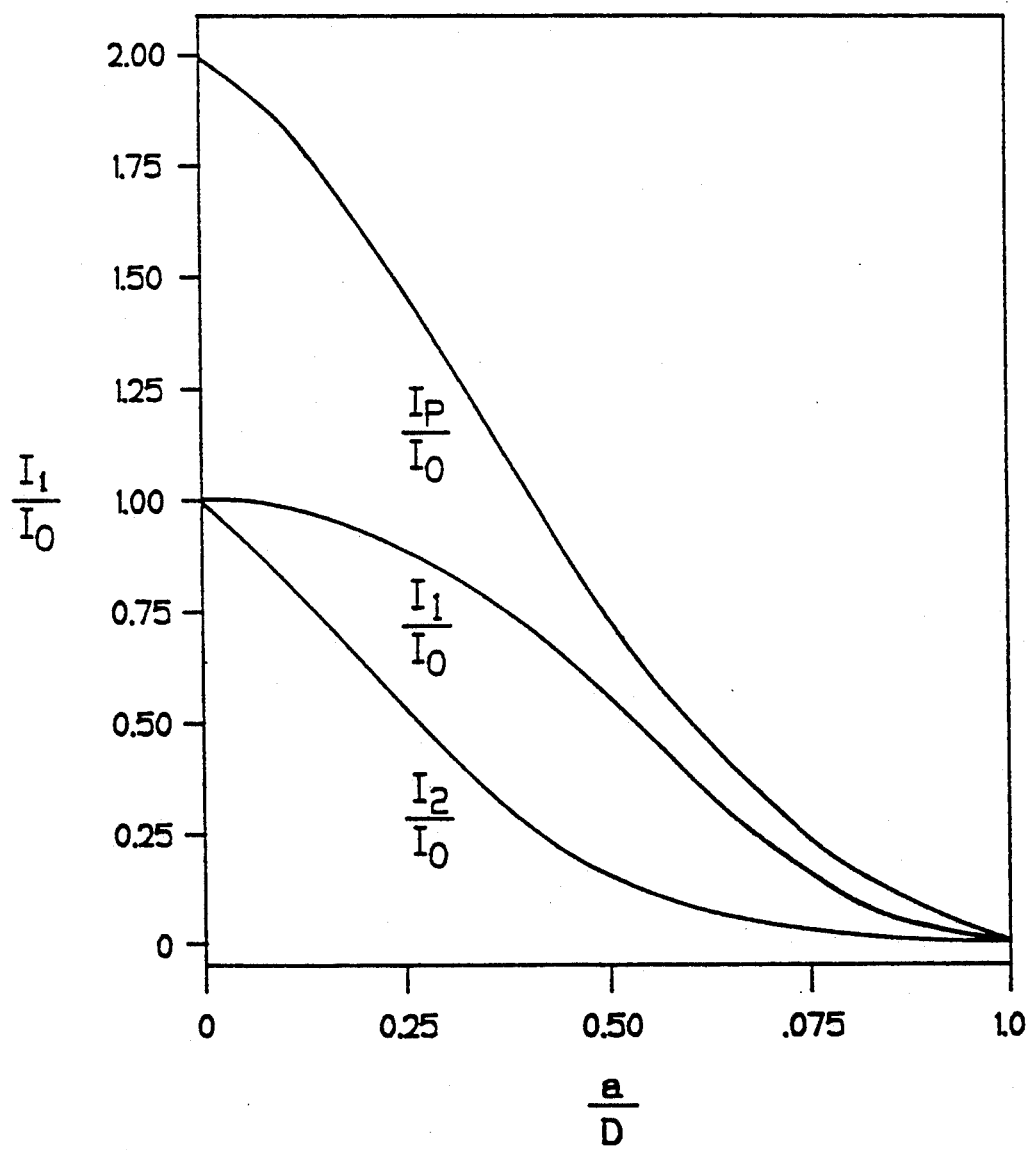
FIG. 7 is a plot of normalized diametrical and polar inertias along stiff, soft and polar axes as a function of crack ratio.

The first step in the preferred method of modeling a shaft crack is to calculate the normalized shaft section inertias for a range of crack depths. Inertia $I_1$ for the stiff direction and inertia $I_2$ for the soft direction are normalized using the inertia $I_0$ for the same diameter shaft uncracked. FIG. 7 depicts a plot of such normalized inertias as a function of crack ratio (crack depth a)/(shaft diameter D).

Figure 6:
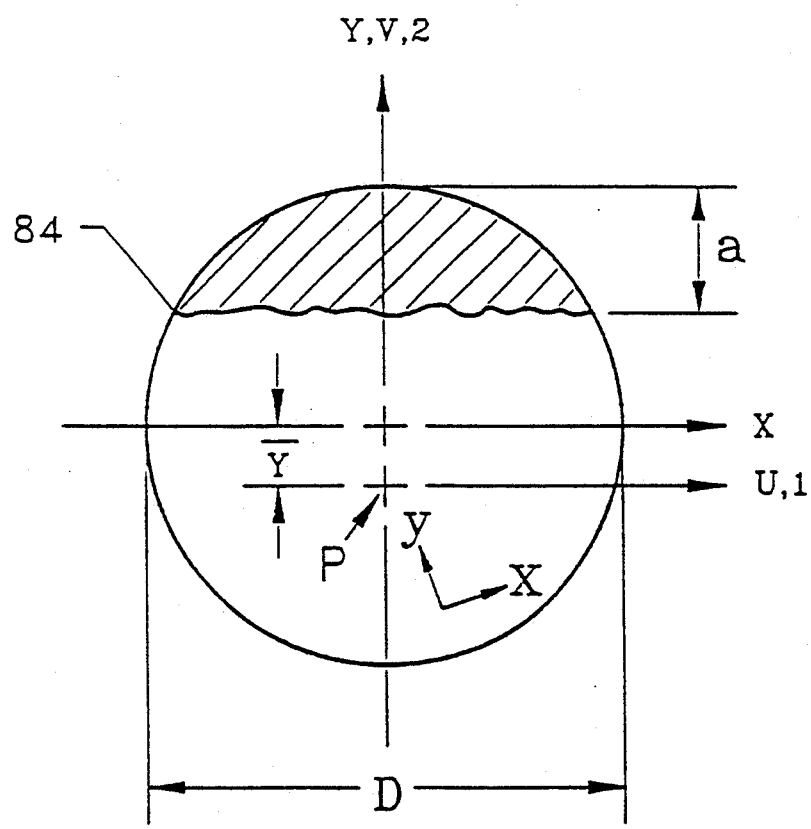
FIG. 6 is a cross-sectional view of an asymmetrically cracked shaft.

The stiffness of a shaft in both torsional and lateral modes is dependent on its section properties, referred to as area second moments or inertia. FIG. 6 depicts a cross section of a cracked shaft. The area inertias can be defined with respect to an arbitrary coordinate system [x,y] by the expressions:

$$Ix = \int y^2 \, dA \tag{2}$$

$$Iy = \int X^2 \, dA \tag{3}$$

$$Ixy = \int XY \, dA \tag{4}$$

$$Ip = \int (X^2 + Y^2) \, dA = I_x + I_y \tag{5}$$

The term Ix relates to stiffness when bending the shaft about the x axis. Similarly, Iy relates to bending the shaft about the y axis. Ix and Iy are always positive, but Ixy can be positive, negative, or zero depending upon the orientation and position of the reference axes. Ip relates to the stiffness when twisting about the z or polar axis.

Refer to the shaft geometry defined in FIG. 6. Let the crack depth be called(a), and the diameter (D). Now construct coordinate system [X,Y] with its origin at the center of the circle representing the uncracked geometry. Rotate [X,Y] such that the Y axis symmetrically bisects the crack. By definition, the term Ixy will vanish if the cross section is symmetric about at least one axis. Therefore, the product of inertia with respect to the [X,Y] system vanishes, i.e. $I_{XY} = 0$.

From classical beam theory, and assuming small deflections, the shaft will bend about its neutral axis. For linear elastic analysis, the neutral axis coincides with the centroidal axis of the section.

As a crack propagates through a shaft, the section neutral axis will migrate in the direction of the crack wave front. At a given crack depth, (a), the neutral axis shifts to point P. A new set of coordinate axes is drawn parallel to [X,Y] and through P. This set of axes is referred to as the Primary Axes [U,V] for the given crack depth. Note that the section is still symmetrical about the V axis, so $I_{UV} = O$. The distance $\overline{Y}$ between the points O and P is defined as:

$$\overline{Y} = \int Y \, dA / \int dA \tag{6}$$

evaluated over the internal region of the cracked section, and with respect to [X,Y].

It is usual to refer to the principal values of section properties, which are the maximum and minimum possible values for $I_U$ and $I_V$, and where $I_{UV}$ must vanish. These properties are usually denoted as $I_1$ and $I_2$ where (with respect to [U,V]):

$$I_1 = \int V^2 \, dU \, dV \tag{7}$$

$$I_2 = \int U^2 \, dU \, dV \tag{8}$$

$$I_{12} = \int UV \, dU \, dV = O \tag{9}$$

While the equations (7), (8), and (9) provide a precise mathematical definition of the Second Area Moments, evaluation of the integrals as defined can be tedious, even for the simple cracked shaft geometry. It can be shown that the inertia terms with respect to a given set of axes can be evaluated with respect to a second set of axes:

$$I^{[UV]} = I^{[XY]} + Ad^2 \tag{10}$$

where:

$I^{[UV]}$ = Inertial components with respect to primary axes [UV] \hfill (11)

$I^{[XY]}$ = Inertial components with respect to centroidal axes [XY] \hfill (12)

where [X,Y] is parallel to [U,V]
A = Area of cross section
d = Distance between parallel axes (X,U) for $I_V$
or
(Y,V) for $I_U$.

For the conditions shown in FIG. 6, (d) corresponds to the distance between the X and U axes, or:

$$d = \overline{Y} \tag{13}$$

Now it can be stated that the principal second moments are:

$$I_1 = I_U = I_x + A Y^2 \tag{14}$$

$$I_2 = I_Y = +A \, (O)^2 = I_Y \tag{15}$$

where:

$$I_X = \int Y^2 \, dX \, dy \tag{16}$$

$$I_Y = \int X^2 \, dX \, dy \tag{17}$$

It is still necessary to evaluate the expressions for $I_X$ and $I_Y$ on the domain by the cracked shaft. The above integrals can be solved using a summation of integrals over continuous subdomains:

$$I(X,Y) = I^1(X,Y) + I^2(X,Y) + I^3(X,Y) \quad (18)$$

where:

$$I^1(X,Y) = \int_{-R}^{-t} \int_{-W(X)}^{W(X)} (\xi) \, dY dX \quad (19)$$

$$I^2(X,Y) = \int_{-t}^{t} \int_{-W(X)}^{h} (\xi) \, dY dX \quad (20)$$

$$I^3(X,Y) = \int_{t}^{R} \int_{-W(X)}^{W(X)} (\xi) \, dY dX \text{ and,} \quad (21)$$

where:

$$W(x) = (R^2 - X^2); \ t = \sqrt{a(D-a)} \ ; R = d/2; h = R - a$$

and $\xi = Y^2$ to evaluate $I_x$, or $\xi = X^2$ to evaluate $I_y$.

This technique, while mathematically precise is usually inconvenient. Therefore, a summation of components is used which states that:

$$I_x = \sum_i (Ix^i + A^i y_i^2) \quad (22)$$

$$I_y = \sum_i (Iy^i + A^i x_i^2) \quad (23)$$

where:
Ix$_i$, Iy$_i$ are second moments with respect to component centroids
A$^i$ = area of component, positive or negative
x$_i$, y$_i$ = distance from [X,Y] system to component's centroidal coordinate system.

In summary, the principal second moments for the cracked shaft are computed using the parallel axis theorem and method of components. The area and centroidal distances Y$_i$ change with varying crack depth, necessitating many calculations. A computer program can be utilized to evaluate the expression over the range of interest. A map of three curves can be generated in dimensionless form to represent all cases. The results of these calculations are shown in FIG. 7.

The next step in the preferred manner of modeling the shaft crack is to calculate an equivalent right circular diameter D$_{eq}$ for each shaft section inertia in each respective direction, i.e. along the soft and stiff axes for lateral analysis, and along the polar axis for torsional analysis, in accordance with the following relationships:

$$D_{eqx} = \sqrt[4]{\frac{I_x \cdot 64}{\pi}} \quad (24)$$

-continued $$D_{eqy} = \sqrt[4]{\frac{I_y \cdot 64}{\pi}} \quad (25)$$

$$D_{eqz} = \sqrt[4]{\frac{(I_x + I_y) \cdot 32}{\pi}} \quad (26)$$

An effective length L representing the axial extent of the shaft effected by the crack is then computed in accordance with the following formula:

$$L = 2(a)(\tan 53°) \quad (27)$$

Figure 8:
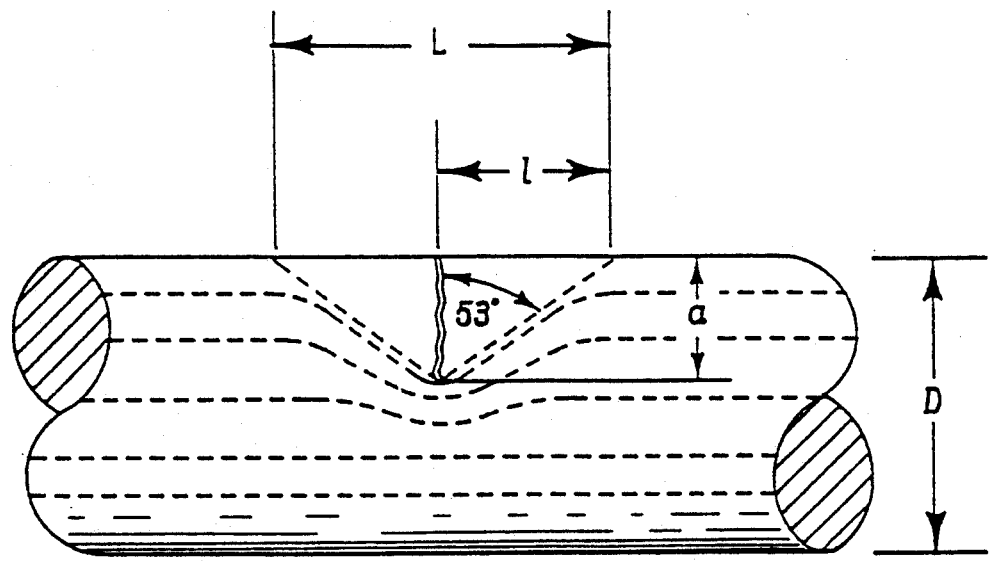
FIG. 8 is a schematic illustration of the lines of stress associated with a shaft crack and the dimensions used to calculate the effective length when modeling an asymmetric crack.

The effective length relationship is illustrated in FIG. 8 and the theory underlying this approach is described in a paper by B. Grabowski entitled "The Vibrational Behavior of a Turbine Rotor Containing a Transverse Crack", Transactions of the ASME Journal of Mechanical Design, Vol. 102, pp. 140-146, Jan. 1980. A range of angles could be used to determine the effective length but 53° appears to provide good results.

As shown in FIG. 8, lines of constant stress in the shaft are redirected due to the existence of the crack. An enhanced crack modeling approach which approximates the flow of stress through the shaft in the area of the crack will now be described with reference to FIGS. 8 and 8a. For a given crack ratio a/D, the shaft is remodeled over the effective crack length L. The remodeling includes calculating moments of inertia "I(new)$_i$" for each station "i" along the effective crack length according to equations 2, 3, and 5.

Each inertia for each station along the effective crack length is then replaced by a value "I$_i$" proportionate to its distance from the crack "C". I$_i$ being determined in accordance with the following equation:

$$I_i = I(\text{old})_i - (|(l_i - (L/2))/(L/2)| \cdot (I(\text{old})_i - I(\text{new})_i))$$

where I(old)$_i$ is a local inertia value of the shaft station "i" for an uncracked shaft, and l$_i$ is the local distance of the station "i" from the suspected crack location "C".

Figure 8A:
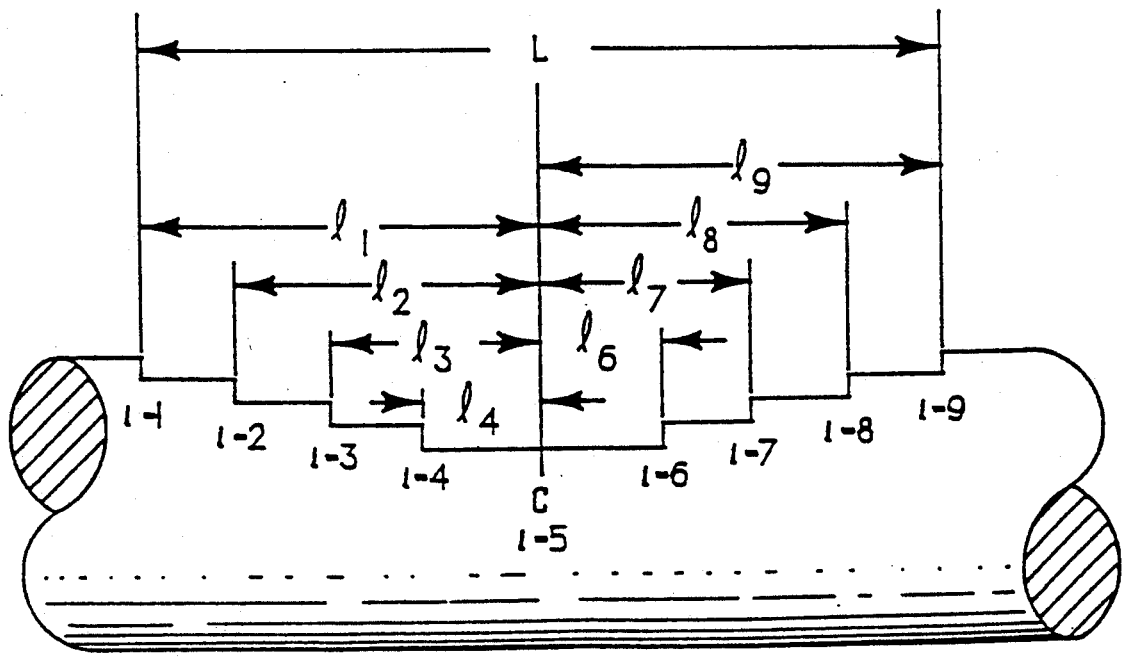
FIG. 8a is a schematic illustration useful in understanding an enhanced crack modeling feature of the present invention.

For the simple case of a right circular cylinder as shown in FIG. 8a, the above equation reduces to:

$$I_i = I_1 - (|(l_i - (L/2))/(L/2)| \cdot (I_1 - I_5))$$

When the crack modeling procedure is performed on a straight shaft, the moments of inertia I$_i$ represent those of a straight shaft with flat steps starting at a length $-L/2$ from the crack, increasing in depth until the suspected crack location is reached, then gradually stepping up to meet the original diameter at a length $+L/2$ from the crack location as shown in FIG. 8a.

The torque in a shaft element is given by:

$$T = \frac{\theta G I_p}{L} \quad (28)$$

where
$\theta$ is the angle of twist,
G is the shear modulus of elasticity,
L is the shaft element length, and
I$_p$ is the polar moment of inertia as defined by equation (5) above.

According to the classical theory of strength of materials, the terms on the right hand side of equation (28) other than $\theta$, are referred to as the torsional spring constant, K. Equation (28) may therefore be rewritten as:

$$T = K\theta \qquad (29)$$

Hence, the asymmetric shaft properties combine to give a single torsional spring constant. One can observe that the torsional natural frequencies will exhibit downward shifts (but not splits) due to the asymmetric reduction in section properties $I_x$ and $I_y$.

The original structural dynamics model of the shaft operating system is modified at the suspected axial location of the crack using the equivalent diameter and effective length for the stiff and soft axes in the lateral analysis and for the polar axis in the torsional analysis, or the results of the enhanced crack modeling approach described above. From this modified model, the operating shaft system's new lateral and/or torsional natural frequencies and mode shapes for each direction, for a range of crack depths, can be derived and a plot of the new lateral and torsional natural frequencies as a function of crack ratio (a/D) made.

Figure 9:
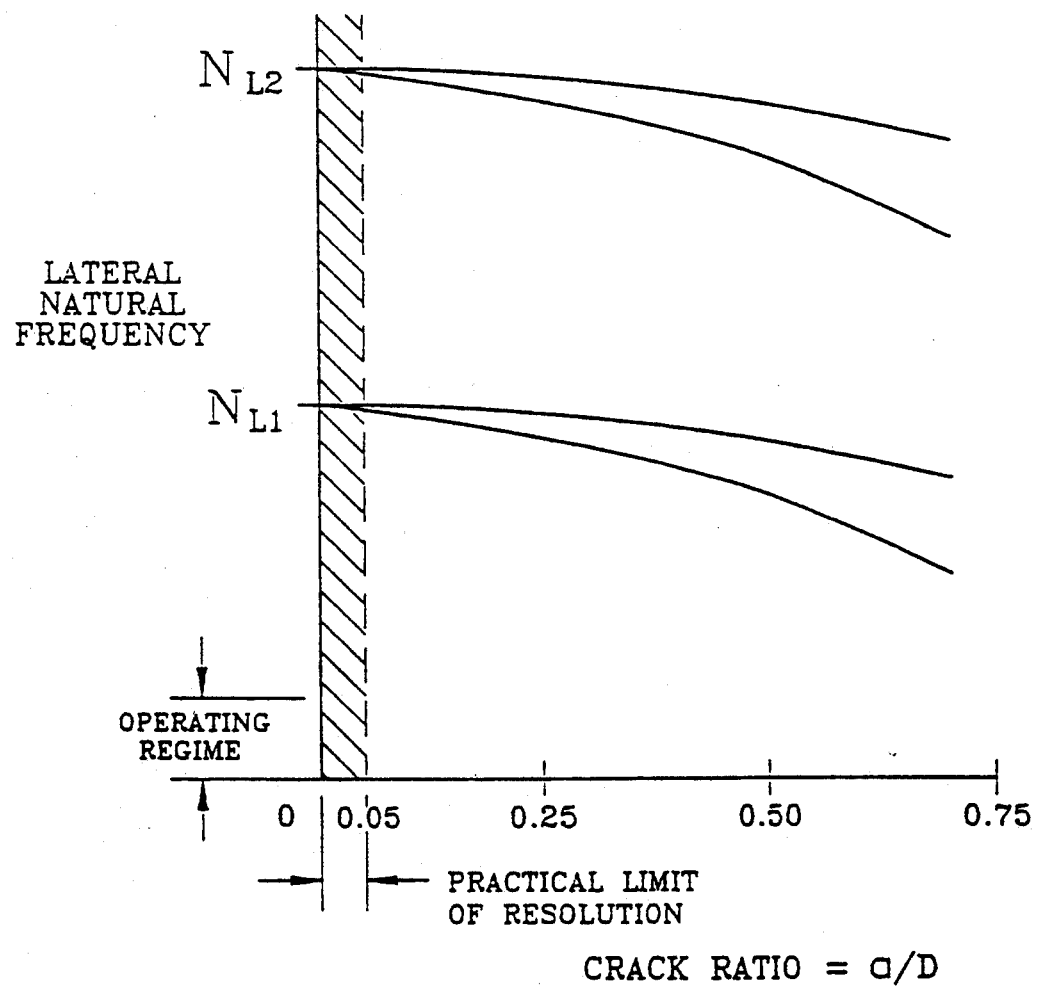
FIG. 9 is a plot illustrating the downward shift and split of shaft lateral natural frequencies as a function of crack ratio.

FIG. 9 presents such a plot for two lateral natural frequencies $N_{L1}$ and $N_{L2}$. The effect of the modeled crack on other lateral natural frequencies could similarly be plotted. Lateral natural frequencies for the uncracked operating shaft are plotted along the abscissa and crack ratio is plotted along the ordinate in FIG. 9. As shown, the lateral natural frequencies are substantially higher than the operating regime of the RCP, as would be expected with a well designed machine. Cracks having a depth on the order of 5% or less of the local diameter are considered to be below the practical limit of resolution because of the lack of simultaneous mass and stiffness homogeneity in the real world. For example, a pair of keyways in the shaft will exhibit an asymmetry equivalent to a crack ratio of approximately 0.03 which can be corrected for (i.e. subtracted out of the crack ratio parameter) to account for such known asymmetries in applying the present method. Beyond a crack ratio of 0.05, the map of FIG. 9 indicates the predicted split and shift of the lateral natural frequencies caused by the introduction of the crack in the model. As the severity of the crack increases, the spread between the two new frequencies becomes more pronounced. The calculated shift and split of a lateral natural frequency of interest for a particular suspected axial location of a crack, as derived from the modified model, can be correlated with actual lateral natural frequency measurements taken on the operating shaft system to determine the presence and size of a crack in the shaft.

Figure 10:
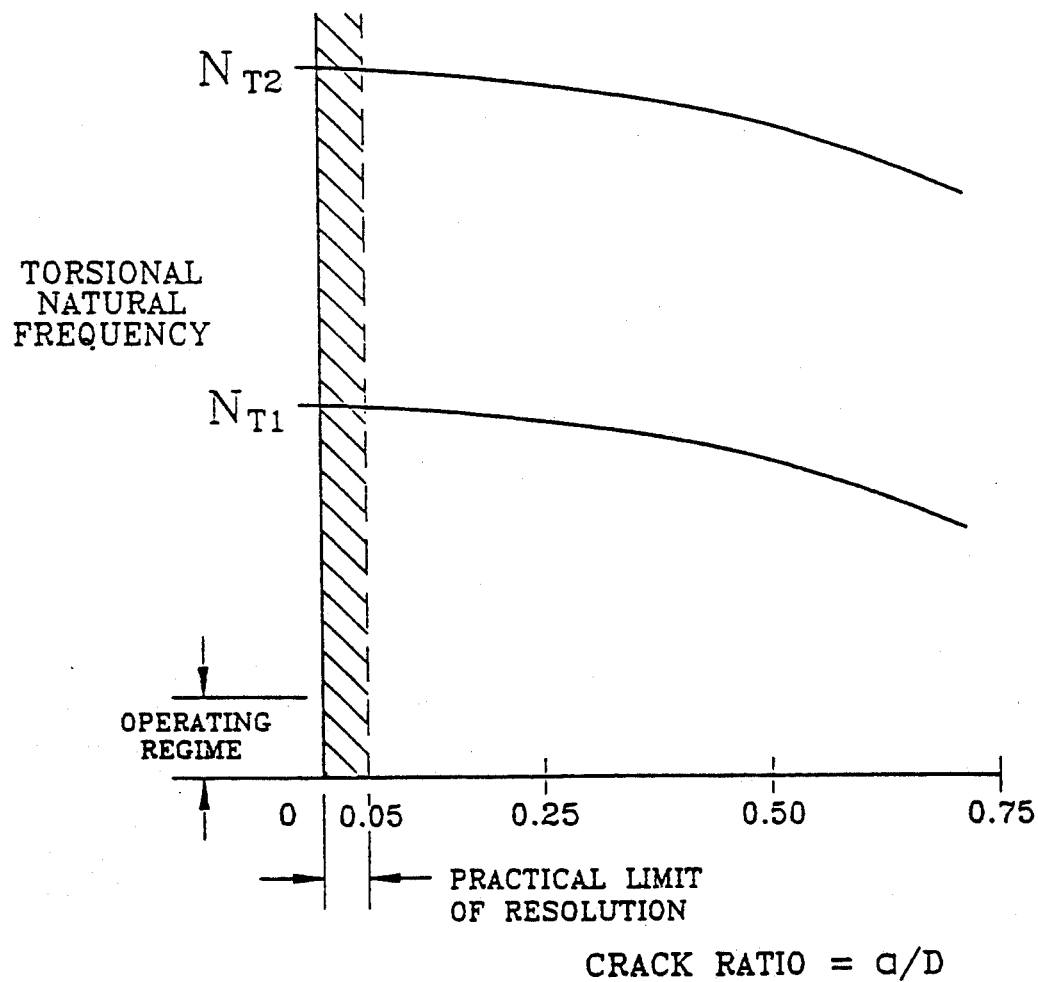
FIG. 10 is a plot illustrating the downward shift of shaft torsional natural frequencies as a function of crack ratio.

The map of FIG. 10 indicates the predicted shift of the torsional natural frequencies $N_{T1}$ and $N_{T2}$ caused by the introduction of the crack in the model. As the severity of the crack increases, the shift of the frequencies becomes more pronounced. The calculated shift of a torsional natural frequency of interest for a particular suspected axial location of a crack, as derived from the modified model, can be correlated with actual torsional natural frequency, measured as illustrated in FIG. 11, to determine the presence and size of a crack in the shaft.

Figure 11:
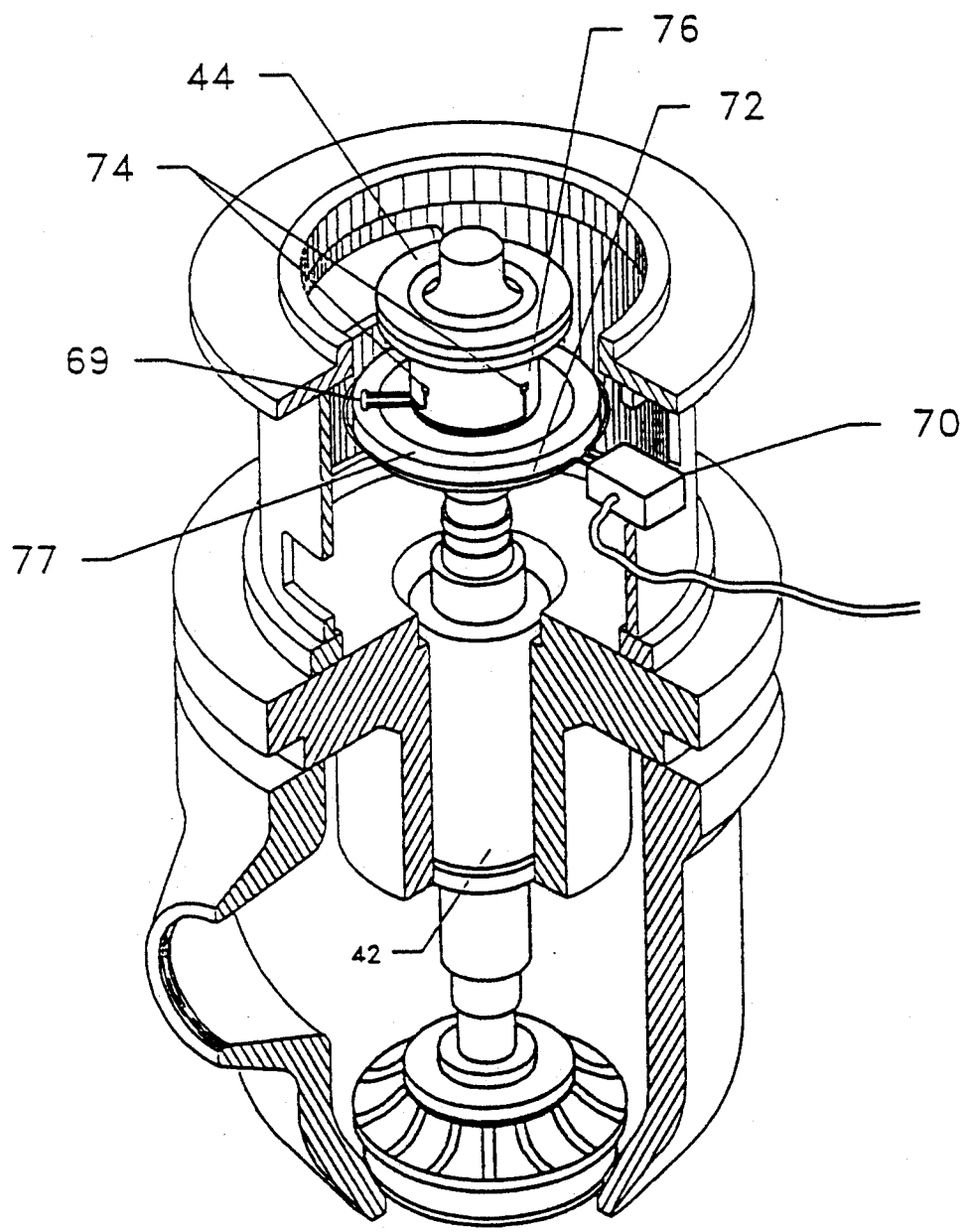
FIG. 11 is a partially cut-away sketch of an exemplary instrumentation arrangement for testing a reactor coolant pump operating shaft system in accordance with the principles of the present invention.

FIG. 11 illustrates exemplary test equipment which can be used to measure the actual lateral and/or torsional natural frequencies of the operating shaft system of the RCP. The shaft system is excited by the operating forces which it experiences during use. The vibrational response of the operating shaft system is preferably measured using multiple sets of strain gages 74 which can be located at any axial position on the shaft. Preferably, this response measurement site is one that affords easy accessibility, i.e. the coupling area.

Figure 12:
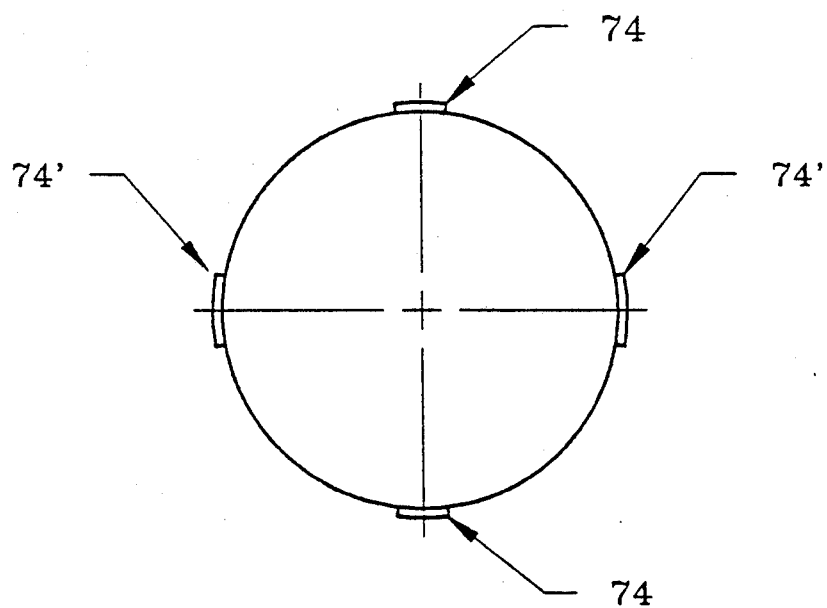
FIG. 12 is a plan view illustrating a preferred circumferential distribution of strain gage sets for use in the test instrumentation arrangement of FIG. 11.

Four strain gage sets 74, circumferentially spaced at 90 degree intervals, as shown in the plan view of FIG. 12, allow simultaneous measurement of lateral and torsional vibrational response. All four strain gage sets are used for measuring actual lateral natural frequencies; only two diametrically opposed sets are needed to measure actual torsional natural frequencies.

Figure 13:
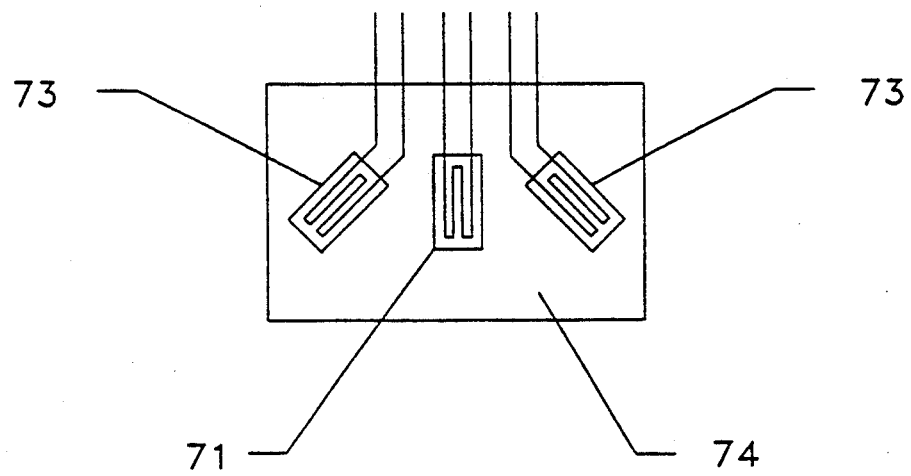
FIG. 13 depicts an exemplary strain gage set.

As illustrated in FIG. 13, each strain gage set 74 preferably includes a central lateral gage 71 aligned with the longitudinal axis of the shaft system, and a pair of torsional gages 73 located on either side of lateral gage 71 at an offset angle of 45 degrees. When suitably powered, the strain gages through a change in resistance provide an electrical signal representative of vibrational response. When four strain gage sets 74 are used in the layout of FIG. 12, all of the lateral gages 71 are activated for lateral analysis but only the torsional gages 73 of either diametrically opposed pair of strain gage sets (e.g. 74') needs to be powered for torsional analysis.

Strain gage sets 74 are glued or otherwise suitably secured to the periphery of the shaft system, for example, on the spacer 76 of coupling spool 44. Optionally, the strain gage sets can be fastened to a spare coupling in an instrumentation shop and then the spare coupling substituted for the coupling that is normally in the machine. This would permit the intricate strain gage fastening work to be done in a clean non-hazardous environment.

As shown in FIG. 11, a fiberglass collar 77 is secured about the periphery of a lower hub of coupling spool 44. Collar 77 includes transmitter/receiver(s) 69 and an embedded antenna (not shown). Transmitter/receiver(s) 69 is electrically connected to the strain gage sets 74 and the embedded antenna. All of these elements rotate with the operating shaft system.

A stationary antenna 72 is mounted in close proximity to collar 77. Antenna 72 is connected through coupler 70 to a strain gage signal conditioner 88. Transmitter/receiver(s) 69 and its associated antenna, in conjunction with stationary antenna 72 and coupler 70, in effect form a short range telemetry system through which a DC voltage is provided to power the strain gages and output AC signals representative of vibrational response measurements are transmitted out of the operating shaft system. The lateral analysis measurements and the torsional analysis measurements can be transmitted on different high frequencies for independent processing and analysis.

The conditioned lateral and torsional output signals are fed, as shown in FIG. 4, to a FFT analyzer 78. The analyzer, in known fashion, provides frequency response spectra, the peaks of which represent the actual natural frequencies. By exciting the shaft through operation and measuring the system frequency response spectra one can observe the variation of the shaft system actual lateral and/or torsional natural frequencies on a continual basis or as frequently as desired. With an operating shaft system, instrumented as described herein, lateral and torsional actual natural frequencies can be measured or monitored simultaneously. Various known equipment can be used to implement the experimental portion of the method of the present invention. As an example, the following test equipment could be used to perform the cracked shaft modal testing:

1. A Zonic 6081Z Two Channel Analysis System With a Zoom Option, and Modal Analysis Software. The Zonic 6081Z multichannel FFT signal processor provides two channels for real time data acquisition with a 40 KHz signal range. The digital zoom analysis processor enables a 20u Hz frequency resolution. The system has a built in 15 megabyte Winchester disk drive and a 320 Kilobyte 3.5 inch micro floppy disk for data back up and storage.

2. Acurex Corporation Model 1200B Universal Data Coupler. This system utilizes a short range telemetry system to provide power to and transmit and receive signals from the strain gages. Separate transmission frequencies are utilized for the torsional and lateral gages so that only one coaxial cable is needed.

3. Micromeasurements Systems manufactures strain gages in a wide assortment of sizes, resistance and configurations (i.e., lateral and torsional). The 350 ohm model provides a substantial signal for measuring the natural frequencies of the shaft system.

By comparing the actual lateral and/or torsional natural frequencies in the regions of the lateral and/or torsional frequencies of interest, with the new system frequencies predicted by the modified model (FIGS. 9 & 10), the presence and severity (i.e. extent of cross sectional reduction as indicated by crack ratio) at the suspected axial location can be determined. Analysis of the response spectra reveals the depth of the crack. Obviously, the test method can be employed in an iterative fashion to check for cracks at different axial locations. Similarly, the method, or just the experimental portion thereof, can be applied over time to monitor crack initiation and/or propagation.

The method of the present invention can be applied to shafts having orientations other than vertical (e.g. horizontal) and to structures other than pumps, such as turbines (steam and gas), generators, motors, and compressors.

From the foregoing description, it will be apparent that a new on-line method for detecting cracks in shafts has been developed which provides earlier detection than prior approaches. The new method allows for the identification of the presence, size and location of a crack anywhere along the shaft even when access to the shaft is limited. The method is performed with the shaft system operating and is applicable to a wide variety of machines.

Although several presently preferred embodiments of the invention have been described and depicted, it will be apparent to those skilled in this art, that various modifications, substitutions, additions, etc. can be made without departing from the spirit of the invention, the scope of which is defined by the claims appended hereto.

What is claimed is:

1. A method for physically testing an operating shaft system and detecting a crack in the operating shaft system under test with the aid of an analytical model, comprising the steps of:

deriving natural frequencies of an uncracked operating shaft system from a multi-station structural dynamics model representative of the operating shaft system under test without cracks, each natural frequency having an associated mode shape representative of shaft system deflection at the natural frequency of each point along a longitudinal axis of the shaft system;

defining a probable axial location of a crack and selecting from among the natural frequencies derived from the model a natural frequency of interest having an associated mode shape which exhibits significant localized bending at said probable axial location of the crack and at a site of vibration response measurement;

modifying the model to include a representation of a crack at said probable axial location;

predicting from said modified model effect of said representation of a crack upon the natural frequency of interest as a function of crack depth;

selecting a site of vibration response measurement on the shaft system;

instrumenting the shaft system at said site of response measurement with a vibration response detector;

subjecting the shaft system to operating force excitation;

detecting the vibrational response of the shaft system to said operating force excitation with said detector;

providing an output signal from said detector representative of said detected vibrational response;

transmitting said output signal to a remote signal processor;

receiving and processing said transmitted output signal and generating therefrom a frequency response spectrum for the operating shaft system;

identifying from said frequency response spectrum an actual natural frequency of the operating shaft system under test in a region near the natural frequency of interest; and determining the existence and severity of a crack in the shaft system under test through comparison of said actual natural frequency to the predicted effect of the representation of a crack upon the natural frequency of interest.

2. The method of claim 1 wherein the modifying step comprises modifying the model to include a representation of an asymmetric crack having a wave front extending parallel to a stiff axis and a crack depth extending along a soft axis; and wherein said step of predicting the effect of the representation of a crack upon a natural frequency of interest comprises calculating a downward shift in the natural frequency of interest as a function of a ratio of crack depth to shaft diameter at said probable axial location.

3. The method of claim 2 wherein said model modifying step comprises representing said crack as a right circular section having an equivalent diameter for shaft section inertia for each of said soft axis and said stiff axis and having an effective length.

4. The method of claim 3 wherein said modifying step comprises:

calculating the shaft section inertia for a range of crack depths at the probable axial location for the stiff axis and for the soft axis;

calculating an equivalent right circular diameter for each shaft section inertia along each of said axes, in accordance with the following equation:

$$D_{eq} = \sqrt[4]{\frac{I \cdot 64}{\pi}}$$

where

"$D_{eq}$" represents the equivalent diameter of a right circular section for a specified axis, and "I" represents the shaft section inertia for a specified axis; and computing the effective length in accordance with the following equation:

$$L = 2(a)(\tan 53°)$$

where

"L" represents the effective length and

"a" represents the crack depth.

5. The method of claim 2 wherein said model modifying step comprises:

calculating moments of inertia $I(new)_i$ for each station i along an effective crack length according to the following equations:

$$I_x = \int y^2 dA$$

$$I_y = \int X^2 dA$$

$$I_p = \int (X^2 + Y^2) dA = I_x + I_y$$

and calculating an inertia value $I_i$ for each station along the effective crack length in accordance with the following equation:

$$I_i = I(old)_i - (|(l_i - (L/2))/(L/2)| \cdot (I(old)_i - I(new)_i))$$

where $I(old)_i$ is a local inertia value of the shaft section i for an uncracked shaft, and $l_i$ is a local distance of a station i from the probable axial location.

6. The method of claim 1 wherein said step of defining a probable axial location of a crack comprises identifying a shaft location at which cracks tend to develop as a result of forces acting on the shaft in accordance with an intended use of the shaft.

7. The method of claim 1 wherein the step of instrumenting the shaft system comprises securing multiple strain gage sets at circumferentially spaced locations to the shaft system.

8. The method of claim 7 wherein vibrational response readings of the strain gage sets are transmitted from the operating shaft system via telemetry.

9. The method of claim 1 wherein the structural dynamics model includes a representation of bearings, seals and support frame.

10. The method of claim 1 wherein the operating shaft system is part of a pump and wherein the structural dynamics model includes the effect of fluid in the pump on the operating shaft system.

11. The method of claim 1 wherein said processing step comprises determining frequency response spectra with a fast Fourier transform analyzer.

12. The method of claim 11 wherein frequency resolution of the natural frequencies derived from the multi-station structural dynamics model of the operating shaft system is at least as great as frequency resolution of the fast Fourier transform analyzer.

13. The method of claim 1 wherein the distance between adjacent stations of the structural dynamics model is no greater than half the local shaft system radius.

14. The method of claim 1 wherein access to the shaft system under test is limited and the site of response measurement is selected to be an easily accessible axial location on the shaft system.

15. The method of claim 1 further comprising the step of verifying the natural frequencies and associated mode shapes derived from the structural dynamics model by subjecting an actual shaft system to a roving force modal analysis.

16. The method of claim 1 wherein the shaft system comprises a rotatable shaft system which is subjected to said operating force excitation while the shaft system is rotating.

17. The method of claim 1 wherein said operating force excitation includes a torsional excitation of the operating shaft system and said detected response comprises a torsional vibrational response.

18. The method of claim 17 wherein the modifying step comprises modifying the model to include a representation of an asymmetric crack having a wave front extending parallel to a stiff axis and a crack depth extending along a soft axis; and wherein said step of: predicting the effect of the representation of a crack upon the natural frequency of interest comprises calculating a downward shift in the natural frequency of interest as a function of a ratio of crack depth to shaft diameter at said probable axial location.

19. The method of claim 18 wherein said model modifying step comprises representing said crack as a right circular section having an equivalent diameter for shaft section inertia for a polar axis extending longitudinally through the center of said shaft system and having an effective length; and wherein said modifying step comprises:

calculating the shaft section inertia for a range of crack depths at the probable axial location for the stiff axis and for the soft axis;

calculating an equivalent right circular diameter for each shaft section inertia along the polar axis, in accordance with the following equation:

$$D_{eqz} = \sqrt[4]{\frac{(I_x + I_y) \cdot 32}{\pi}}$$

where

"$D_{eqz}$" represents the equivalent diameter of a right circular section for torsional analysis, "Ix" represents the shaft section inertia for the stiff axis, "Iy" represents the shaft section inertia for the soft axis, and "Ip" represents the shaft polar moment of inertia; and computing the effective length in accordance with the following equation:

$$L = 2(a)(\tan 53°)$$

where

"L" represents the effective length and

"a" represents the crack depth.

20. The method of claim 17 wherein said model modifying step comprises:

calculating moments of inertia $I(new)_i$ for each station i along an effective crack length according to the following equations:

$$Ix = \int y^2 dA$$

$$Iy = \int X^2 dA$$

$$Ip = \int (X^2 + Y^2) dA = I_x + I_y$$

and calculating an inertia value $I_i$ for each station along the effective crack length in accordance with the following equation:

$$I_i = I(\text{old})_i - (|(l_i - (L/2))/(L/2)| \cdot (I(\text{old})_i - I(\text{new})_i))$$

where $I(\text{old})_i$ is a local inertia value of the shaft section i for an uncracked shaft, and $l_i$ is a local distance of a station i from the probable axial location.

21. The method of claim 1 wherein the operating force excitation includes a lateral excitation of the operating shaft system and said detected response comprises a lateral vibrational response.

22. The method of claim 21 wherein the modifying step comprises modifying the model to include a representation of an asymmetric crack having a wave front extending parallel to a stiff axis and a crack depth extending along a soft axis; and wherein said step of predicting the effect of the representation of a crack upon the natural frequency of interest comprises calculating a downward shift and a split in the natural frequency of interest as a function of a ratio of crack depth to shaft diameter at said probable axial location for lateral analysis.

23. The method of claim 22 wherein the vibrational response is detected along multiple diameters of the operating shaft system.

24. The method of claim 22 wherein said model modifying step comprises:

calculating moments of inertia $I(new)_i$ for each station i along an effective crack length according to the following equations:

$$Ix = \int y^2 dA$$

$$Iy = \int X^2 dA$$

$$Ip = \int (X^2 + Y^2) dA = I_x + I_y$$

and calculating an inertia value $I_i$ for each station along the effective crack length in accordance with the following equation:

$$I_i = I(\text{old})_i - (|(l_i - (L/2))/(L/2)| \cdot (I(\text{old})_i - I(\text{new})_i))$$

where $I(\text{old})_i$ is a local inertia value of the shaft section i for an uncracked shaft, and $l_i$ is a local distance of a station i from the probable axial location.

25. A method for physically testing an operating shaft system and detecting a crack in the operating shaft system under test, comprising the steps of:

determining from a multi-station analytical model of the operating shaft system a natural frequency of interest for a crack at a designated location on the shaft system, and predicting a shift of said natural frequency of interest as a function of crack depth;

instrumenting said shaft system to measure vibrational response thereof;

subjecting said instrumented shaft system to vibration inducing operating force excitation;

measuring the vibrational response of the shaft system to said vibration inducing operating force excitation;

generating a frequency response spectrum for the operating shaft system from said measured vibrational response;

identifying from said frequency response spectrum an actual natural frequency of said operating shaft system in a region near the natural frequency of interest; and determining existence of a crack in the shaft system and severity thereof from a comparison of said actual natural frequency to the predicted shift of the natural frequency of interest.

26. The method of claim 25 wherein the step of measuring the vibrational response of the shaft system comprises taking a measurement of torsional vibrational response of the operating shaft system.

27. A method for detecting a crack in an operating shaft system under test, comprising the steps of:

(a) selecting a first natural frequency of interest for the operating shaft system for lateral analysis, the natural frequency of interest having an associated mode shape which exhibits a region of high bending at a designated location of a crack and at a site of response measurement on the shaft system, and predicting a split and shift of said first natural frequency of interest as a function of crack depth;

(b) selecting a second natural frequency of interest for the operating shaft system for torsional analysis, and predicting a downward shift of said second natural frequency of interest as a function of crack depth;

(c) subjecting the operating shaft system to a vibration inducing operating force excitation;

(d) measuring vibrational response of the operating shaft system at said site of response measurement to said operating force excitation;

(e) generating frequency response spectra from said measured vibrational response;

(f) identifying from said frequency response spectra actual natural frequencies for lateral analysis in a region of the first natural frequency of interest;

(g) identifying from said frequency response spectra an actual natural frequency for torsional analysis in the region of the second natural frequency of interest;

(h) comparing said actual natural frequencies for lateral analysis to the predicted split and shift of the first natural frequency of interest to determine a correlation therebetween;

(i) comparing said actual natural frequency for torsional analysis to the predicted downward shift of the second natural frequency of interest to determine a correlation therebetween; and (j) determining the presence and severity of a crack in said operating shaft system based on results of said correlations.

28. The method of claim 27 wherein vibrational response measurement readings for lateral analysis and for torsional analysis are taken simultaneously.

29. A method for physically testing an operating shaft system and detecting a crack in the operating shaft system under test, comprising the steps of:
- instrumenting the shaft system to measure vibrational response thereof at a site of response measurement;
- subjecting the shaft system to vibration inducing operating force excitation;
- measuring vibrational response of the operating shaft system to said operating force excitation at said site of response measurement and providing an electrical signal representative of said measured vibrational response;
- processing said electrical signal to identify an actual natural frequency of the operating shaft system under test in a region near a natural frequency of interest, said natural frequency of interest having been derived from a multi-station structural dynamics model representative of the operating shaft system under test without cracks, said natural frequency of interest having an associated mode shape which exhibits a region of high bending at a probable axial location of a crack and at the site of response measurement; and
- determining the presence of a crack in said operating shaft system by comparing said actual natural frequency to one of (a) the natural frequency of interest, and (b) an earlier similarly determined actual natural frequency of the operating shaft system.

30. The method of claim 29 wherein the vibrational response measured is torsional; and further comprising the step of determining crack depth based upon a difference between the actual natural frequency of the shaft system and the natural frequency of interest.

31. The method of claim 30 wherein the step of determining crack depth comprises correlating said difference with a predicted shift of said natural frequency of interest as a function of crack depth.

32. The method of claim 31 wherein said predicted shift of said natural frequency of interest is derived from the multi-station structural dynamics model modified to include a representation of a crack at said probable axial location.

33. The method of claim 29 wherein the vibrational response measured is lateral;
- wherein said processing step comprises processing said electrical signal representative of said measured vibrational response to determine a pair of actual natural frequencies of the operating shaft system under test in the region near the natural frequency of interest; and
- further comprising the step of determining crack depth based upon frequency differences between said pair of actual natural frequencies and between said pair of actual natural frequencies and the natural frequency of interest.

34. The method of claim 33 wherein said step of determining crack depth comprises correlating said pair of actual natural frequencies to a predicted shift and split in the natural frequency of interest as a function of crack depth.

35. The method of claim 34 wherein said predicted shift and split in the natural frequency of interest is derived from the multi-station structural dynamics model modified to include a representation of a crack at said probable axial location.

36. In a method for determining presence and severity of a crack in an operating shaft system under test, an improvement comprising the following sequence of steps:
- deriving natural frequencies of an uncracked operating shaft system, each natural frequency having an associated mode shape representative of shaft system deflection at the natural frequency;
- defining a probable axial location of a crack and selecting from among said natural frequencies a natural frequency of interest having an associated mode shape which exhibits significant localized bending at said probable axial location of the crack and at a site of response measurement; and
- predicting effect of a crack at said probable axial location upon the natural frequency of interest as a function of crack depth, whereby presence and severity of a crack in the operating shaft system under test can be determined by comparing a measured actual natural frequency of the operating shaft system under test in a region near the natural frequency of interest to the predicted effect of the representation of the crack upon the natural frequency of interest.

37. The method of claim 36 wherein:
- the natural frequencies of the uncracked operating shaft system are derived from a multi-station structural dynamics model of the operating shaft system under test without cracks; and
- the effect of a crack at said probable axial location is predicted from said model modified to include a representation of a crack at said location.

38. A method for detecting a crack in an operating shaft system under test, comprising the steps of:
- subjecting the shaft system to a vibration inducing operating force excitation;
- measuring vibrational response of the shaft system to said operating force excitation at a site of response measurement;
- generating a frequency response spectrum for the operating shaft system from said measured vibrational response;
- identifying in said frequency response spectrum an actual natural frequency in a region near a natural frequency of interest, said natural frequency of interest having been selected on the basis that it has an associated mode shape which exhibits significant localized bending at a probable axial location of a crack and at the site of response measurement; and
- determining existence of a crack in the operating shaft system by comparing said actual natural frequency to the natural frequency of interest.

39. The method of claim 38 wherein said natural frequency of interest is derived from a multi-station structural dynamics model representative of the operating shaft system under test without cracks.

40. The method of claim 39 wherein said shaft system under test is rotating; said excitation includes a torsional component; and said comparing step comprises determining a difference in frequency value between the actual natural frequency and the natural frequency of interest.

41. The method of claim 40 further comprising the step of correlating said difference with a predicted shift in the natural frequency of interest as a function of crack depth.

42. The method of claim 38 wherein said shaft system under test is rotating; said identifying step comprises identifying a pair of actual natural frequencies near the natural frequency of interest; and said comparing step comprises determining differences in frequency value between said pair of actual natural frequencies and between said pair of actual natural frequencies and said natural frequency of interest.

43. The method of claim 42 further comprising the step of correlating said differences with a predicted shift and split of the natural frequency of interest as a function of crack depth.

* * * * *